US00PP09290P

United States Patent [19]

Olesen

[11] Patent Number: Plant 9,290

[45] Date of Patent: Sep. 19, 1995

[54] CLEMATIS NAMED 'VINO'

[75] Inventor: Mogens N. Olesen, Fredensborg, Denmark

[73] Assignee: The Guernsey Clematis Nursery Limited, United Kingdom

[21] Appl. No.: 331,038

[22] Filed: Oct. 28, 1994

[51] Int. Cl.[6] ..... A01H 5/00

[52] U.S. Cl. ..... Plt./54.1

[58] Field of Search ..... Plt. 54.1, 68.1

*Primary Examiner*—James R. Feyrer

*Attorney, Agent, or Firm*—Christie, Parker & Hale

[57] ABSTRACT

A new variety of clematis having large red/purple flowers with contrasting yellow anthers and slightly twisting leaves.

1 Drawing Sheet

BACKGROUND OF THE INVENTION

This invention relates to a new and distinct variety of Clematis. The varietal denomination of the new variety is 'Vino'. It was discovered as a seedling in my controlled planting of cultivated plants in nursery at Fredensborg, Denmark and its parents are not known.

SUMMARY OF THE INVENTION

Among the features which distinguish the new variety from other presently available and known commercial clematis cultivars are the following combination of characteristics including large red/purple flowers with contrasting yellow anthers and slightly twisting leaves. 'Vino' is asexually propagated by vegetative cuttings and asexual reproduction of new variety as performed by vegetative cuttings in Guernsey, Channel Islands, Great Britain, shows that the foregoing and other distinguishing characteristics come true to form and are established and transmitted through succeeding propagations.

BRIEF DESCRIPTION OF THE ILLUSTRATION

The accompanying photographic illustration shows the foliage and flowers of the new variety, with different flowers shown in various stages of maturity. The flower poise, contrasting colors, petal count and petal characteristics are depicted. The domed boss of stamens is shown forming the attractive center of the flowers and the coloration and character of the foliage can be seen beneath the flowers. The coloration shown in the photograph is as nearly correct as is possible in color illustrations of this character. Throughout the specification color values are based upon the *Royal Horticultural Colour Chart,* Royal Horticultural Society of London, England, except where common terms of color definition are employed.

DESCRIPTION OF THE NEW VARIETY

The following description is of clematis plants of the new cultivar grown under glass at Guernsey, Channel Islands, Great Britain throughout the flowering period. Phenotypic expression may vary with environmental, cultural and climatic conditions, as well as differences in conditions of light and soil.

PLANT

A. Form: Upright, climbing or spreading.

B. Growth: Medium growth.

*Height attained.*—About 2 meters to about 3 meters.

C. Foliage: deciduous, compound—tri-folate, sometimes simple.

1. *Size.*—Medium.
2. *Quantity.*—Average.
3. *Color.*—New Foliage: Upper side — near 137B. Underside — near 137C. Old Foliage: Upper side — near 137B. Underside — near 137C.
4. *Shape.*—Lower leaves sometimes simple; normally 3 ovate leaflets in pinnate form.
5. *Texture.*—Upper side — glabrous. Underside — ribbed.
6. *Edge.*—Normal.
7. *Serration.*—None.
8. *Petiole color.*—Top surface — green changing to red with age. Underside — same as top surface.
9. *Stipules.*—None.
10. *Internodes.*—Describe: Cylindrical. Length: About 12 cm to about 17 cm in length.
11. *Resistance to disease.*—Subject to any disease that normally affect clematis but less prone to mildew than some clematis.

D. Wood:

1. *New shoots.*—Color — light green. Bark—smooth.
2. *Old wood.*—Color — reddish brown. Bark — rough.

E. Hardiness: Zone 4–9.

FLOWER

A. Blooming habit: Recurrent.

B. Bud:

1. *Size.*—About 4 cm to about 5 cm.
2. *Form.*—Elliptic to ovate.
3. *Color.*—Green/grey hairy.

C. Sepals: None—tepals only.

D. Peduncle:

1. *Length.*—About 8 cm to about 10 cm.
2. *Aspect.*—Vertical.
3. *Strength.*—Erect.
4. *Color.*—Green, near 143C.

E. Bloom:

1. *Size.*—About 15 cm to about 18 cm.
2. *Borne.*—Singly.
3. *Form.*—Tepals opening to become flat.
4. *Petalage.*—6–8.
5. *Color.*—Outer tepals: Top surface, near 60B. Undersurface — red/purple, lighter than top surface, white main midrib. Base of tepals: White. General Tonality from a distance: Red purple.

6. *Color change.*—As bloom ages, all colors fade and show more violet, color varies throughout the flowering season.

*General tonality at a distance.*—Light red-purple.

F. Tepals:

1. *Texture.*—Medium.
2. *Appearance.*—Top surface — satiny. Under surface — matt.
3. *Form.*—Obovate.
4. *Arrangement.*—Regularly arranged.
5. *Petaloids in center.*—None.
6. *Persistence.*—Tepals persistent.
7. *Fragrance, if any.*—None.
8. *Lasting quality on plant and after cutting.*—About two weeks on plants, lasting only a few days as a cut flower.

REPRODUCTIVE ORGANS

A. Stamens, filaments and anthers:

1. *Arrangement.*—Regularly arranged, but style more prominent than most other clematis, short stamens.
2. *Color.*—Stamens: White base, shading to yellow tip. Filaments: White. Anthers: Yellow.

B. Pollen:

*Color.*—Cream.

C. Styles: Bunched, even, longer than stamens.

D. Stigmas:

*Color.*—Cream.

E. Hips:

Shape.—None.

I claim:

1. A new and distinct variety of clematis substantially as described and illustrated herein.

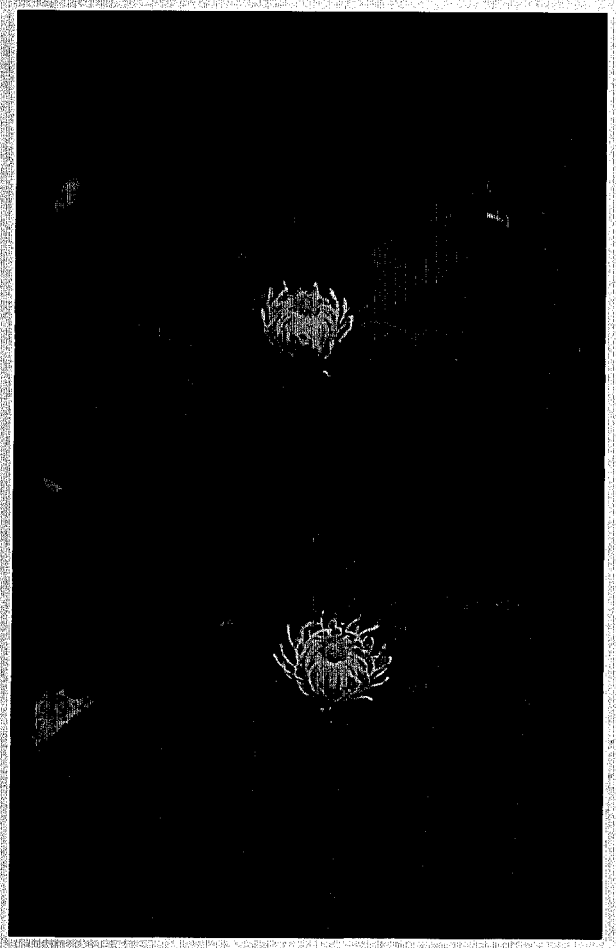

* * * * *